United States Patent [19]

Mathew

[11] Patent Number: 4,922,017

[45] Date of Patent: May 1, 1990

[54] PROCESS FOR PRODUCTION OF AROMATIC ALDOXIMES

[75] Inventor: Chempolil T. Mathew, Randolph, N.J.

[73] Assignee: Allied-Signal Inc., Morris Township, Morris County, N.J.

[21] Appl. No.: 208,438

[22] Filed: Jun. 20, 1988

[51] Int. Cl.$^5$ ............................................. C07C 131/00
[52] U.S. Cl. ...................................... 564/265; 564/259
[58] Field of Search ................. 564/259, 265; 568/347

[56] References Cited

U.S. PATENT DOCUMENTS

| | | | |
|---|---|---|---|
| 3,081,347 | 3/1963 | Leary | 564/259 |
| 3,429,920 | 2/1969 | de Rooij | 564/259 |
| 3,624,157 | 11/1971 | Ingwalson et al. | 568/437 |
| 4,323,706 | 4/1982 | Bonfield et al. | 564/259 |

FOREIGN PATENT DOCUMENTS 56-166131  12/1981  Japan ..................................... 56/437

OTHER PUBLICATIONS

E. Muller, Methoden der Organishchen Chemie, 85–90 (Houben–Weyl, 4th ed. 1968).

*Primary Examiner*—James H. Reamer
*Attorney, Agent, or Firm*—Colleen D. Szuch; Melanie L. Brown; Jay P. Friedenson

[57] ABSTRACT

A process for preparing an aromatic aldoxime, such as benzaldehyde oxime, by reacting the corresponding, $\alpha,\alpha$-dihalide, such as benzal chloride, with a hydroxylamine salt in the presence of an excess of an aqueous base sufficient to maintain the product oxime in solution. Organic impurities may be phase separated from the reaction mixture. Thereafter, the aqueous solution containing product oxime is neutralized to separate an oxime phase, which may be recovered by decanting or solvent extraction.

12 Claims, No Drawings

PROCESS FOR PRODUCTION OF AROMATIC ALDOXIMES

DESCRIPTION

This invention relates generally to the production of aromatic aldoximes and particularly to the production of benzaldehyde oxime.

BACKGROUND OF THE INVENTION

The preparation of oximes is generally described in U.S. Pat. No. 4,323,706 directed to production of acetaldehyde oxime as follows:

"Oximes are conventionally prepared by oximating a ketone or aldehyde with an aqueous hydroxylamine-containing solution. The oxime is then recovered from the aqueous solution . . . Many oximes are easily recovered from the aqueous oximation reaction mixture because the relatively water-insoluble oxime forms a separate phase from the aqueous phase, and may be separated by decantation or the like".

Acetaldehyde oxime is thereafter described as presenting a unique recovery problem because is relatively water - soluble and therefore cannot be phase-separated.

Another method of preparation of oximes is shown in several patents issued to McBee, (U.S. Pat. Nos. 3,141,043, 3,462,488 and 3,459,802) which employ hydroxylamines in methanol solutions to carry out the oximation reaction. The oxime may be extracted with ether and recovered.

Generally, aromatic aldoximes are prepared by the reaction of aromatic aldehydes with hydroxylamine generated from hydroxylamine salts.

The present invention relates to a new and simple method for preparation of aromatic aldoximes by reaction of the correspondinq aromatic $\alpha,\alpha$-dihalides with hydroxylamine salts and which provides high yields of the oxime product and simple recovery of a high purity product, even if relatively impure aromatic dihalides are used as a feedstock.

Benzaldehyde oxime is usually prepared from benzaldehyde, as described above in the excerpt from the '706 patent. While benzaldehyde can be prepared from hydrolysis of benzal chloride, the reaction product would be separated from the by product hydrochloric acid and purified before being converted to the oxime. In one embodiment of the present invention, benzaldehyde oxime is made directly from benzal chloride, even if crude and unpurified, thus avoiding the multiple-step process cf the art.

SUMMARY OF THE INVENTION

Aromatic aldoximes are prepared by reacting aromatic $\alpha,\alpha$-dihalides with a hydroxylamine salt, such as hydroxylamine sulfate, in the presence of an excess of an aqueous base, preferably an inorganic base. Use of excess of aqueous base ls especially useful when the $\alpha,\alpha$-dihalide contains organic impurities. Any organic impurities which may be present in the aromatic $\alpha,\alpha$-dihalide form a separate layer and may be decanted, while the product aromatic aldoxime remains in the basic aqueous phase. When that phase is separated and then neutralized, as by adding aqueous hydrochloric acid, the aromatic aldoxime separates as a distinct phase and may be recovered by filtering, decanting of solvent extraction.

In one embodiment benzaldehyde oxime is made from benzal chloride in a solution containing sufficient aqueous sodium hydroxide to provide a reaction mixture having a pH of about 12. The aqueous layer containing the oxime product is separated and then neutralized to a pH of about 7 by adding aqueous hydrochloric acid which separates the benzaldehyde oxime product.

DESCRIPTION OF THE PREPARED EMBODIMENTS

Reagents

Aromatic aldoximes may be prepared according to the invention from the corresponding $\alpha,\alpha$-dihalides, as represented by the following formula:

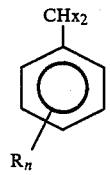

where:
x = Cl, Br, I
R = H, alkyl, alkoxyalkyl, aryl, aralkyl, alkylthio, aryloxy, fluorine perfluoroalkyl
n = 1 to 5

In a particularly preferred embodiment the starting compound is benzal chloride, but other substituted aromatic dihalides may serve as the oxime precursor. Examples of such compounds are benzal bromide, 4-fluorobenzal chloride, 4-methyl benzal bromide, 3-fluorobenzal bromide, 4-methyl benzal chloride, 3-methylthiobenzal chloride, 3-fluorobenzal chloride, 4-trifluoromethyl benzal chloride, 4-methyl-2-$\alpha$-$\alpha$-dibromomethyl naphthalene, 1-$\alpha$-$\alpha$-dichloromethyl naphthalene, 2-$\alpha$-$\alpha$-dichloro methyl naphthalene, 4-methylthio benzal bromide 4-methoxy methyl benzal chloride, 4-phenyl benzal chloride, 4-$\alpha$-$\alpha$-dichloro methyl diphenyl ether, 4-benzyl benzal chlorlde, 2-methoxy benzal bromide, 4-methoxy benzal chloride.

In a preferred embodiment benzal chloride provides the principal starting compound for benzaldehyde oxime. The benzal chloride may be pure or it may be a crude form of benzal chloride contaminated with organic impurities such as benzyl chloride, benzotrichloride and toluene and other analogous hydrocarbons. It is an advantage of the present process that benzaldehyde oxime can be prepared with high purity even from such crude benzal chloride feedstocks. Benzal chloride is typically prepared by chlorlnation of toluene using elemental chlorine.

The hydroxylamine salt may be the sulfate, hydrochloride, phosphate, acetate and the like but preferably the least expensive hydroxyl amine sulfate is used. It may be produced by catalytic reduction of nitric oxide or nitric acid, reduction of a nitrite salt with sulfur dioxide or sulfite and hydrolysis of the hydroxylamine sulfonate thus produced, or hydrolysis of a simple oxime with aqueous inorganic acid.

The reaction is carried out in the presence of an aqueous base preferably an inorqanic base which provides conditions under which the organic impurities, if any of the benzal chloride will be separated as a distinct organic phase while the product oxide retains in the aqueous solution. Various bases may be employed, such as alkali and alkaline-earth metal hydroxide and carbonate but preferably aqueous sodium hydroxide is employed.

Sufficient base will be used to provide a pH of about 9-13, preferably about 12.

Reaction

The reaction may be illustrated by a preferred embodiment as follows:

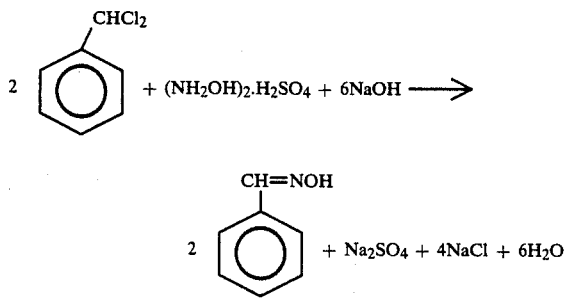

It will be seen that in addition to providing a high pH the sodium hydroxide plays an important role in the reaction by which the aromatic aldoxime is produced. Thus, when reference is made to excess base it is meant that more than the amount required by the stoichiometry of the reaction is used. Since at a neutral pH the reaction mixture will separate the product oxime, sufficient base is used to retain the product in solution until it is to be separated especially in cases where crude aromatic dihalide is used and by-products must be separated. Generally, it has been found that the product will be about 95% pure or more and the yield virtually quantitative.

The reaction may be carried out at atmospheric pressure, although above atmospheric pressures may be used if desirable. The temperature of the reaction will be about 0° to 100° C. preferably 50° to 80° C. The pH during the reaction will be at least 9-14, preferably at least 11-13. Neutralization of the excess base will bring the reaction mixture to a pH of about 6-8 so that the product oxime may be readily separated.

The following examples illustrate the process of the invention.

EXAMPLE 1

A 500 ml 3-neck flask was set up with a thermometer, dropping funnel and a reflux condenser. A magnetic stirring bar was placed in the flask and the flask clamped over a stir-plate.

Sodium Hydroxide solution (80 g; 50% aqueous, 1.0 mol) was placed in the flask and with stirring was mixed with water (50 g). To the solution was added benzal chloride (32.2 g; 0.20 mol), and with continued stirring a solution of hydroxylamine sulfate (21 g; 0.128 mol) in water (150 ml) was added. The two-phase mixture was heated with stirring at 70°-75° C. for a total of 5 hours, by the end of which time the organic phase disappeared. pH of the solution at this point was 12.2, The solution was cooled to 25° C. and treated with hydrochloric acid to bring it to pH 7. A colorless oily phase separated out which was confirmed by comparison with an authentic sample (using gas chromatography and infra red spectroscopy) to be pure (98.1%) benzaldehyde oxime. The yield was 24.1 g (97.7%).

EXAMPLE 2

In a 500 ml 3-neck flask was placed crude benzal chloride (38.2 g: 84.3% pure: 0.20 mol) which was mixed with water (200 ml), sodium hydroxide solution (80 g; 50% solution: 1.0 mol) and hydroxylamine sulfate (34 g; 0.207 mol). The mixture was heated with stirring at 60°-75° C. for 4 hours. After cooling to ambient temperature, toluene (60ml) was added and mixed for 10 minutes. The two-phase mixture was transferred into a 500 ml separatory tunnel and the aqueous phase separated and collected from the bottom. The toluene phase contained virtually all the impurities originally present in the crude benzal chloride sample and was discarded.

The aqueous phase (pH 12.2) was neutralized with hydrochloric acid and benzaldehyde oxime separated on top as an oily layer with a light amber color. This was separated and collected (23.8 g). Gas chromatographic analysis showed that the product was 95.1% pure, the major impurity being toluene. The yield was 93.5%.

EXAMPLE 3

A 250 ml 3-neck flask was fitted with a dropping funnel, thermometer and reflux condenser. A magnetic stirring bar was introduced and the flask was clamped over a stir-plate. Sodium hydroxide (48 g of 50% solution, 0.60 mol) was placed in the flask and mixed With distilled water (32.5 g). With stirring 4-fluorobenzal chloride (21.5 g, 0.12 mol, Aldrich) was introduced using the dropping tunnel. Separately, hydroxylamine sulfate crystals (18.0 g, 0.11 mol) were dissolved in distilled water (61.0 g) in a beaker and the solution was placed in the dropping tunnel. The solution was added to the flask slowly over 5 minutes with stirring, when the temperature rose to 43° C. The contents of the flask (2 liquid phases with the organic phase at the bottom) was then heated over a mantle with stirring at about 80° C. for about 5 hours. A vigorous reaction took place as the heating continued and the organic phase slowly disappeared. At that point the mixture was cooled and neutralized with conc. HCl. A brownish solid collected at the bottom, and this was filtered off (17.2 g). On crystallization from methanol it gave colorless crystalline solid (15.8 g). Yield 94.8%.

By gas chromatography and Infra Red and NMR analyses, the solid was identified to be 4-fluoro benzaldehyde oximes.

EXAMPLE 4

In a 3-neck 250 ml flask fitted with thermometer, reflux condenser and dropping funnel was placed a magnetic stirring bar. A solution of sodium hydroxide (36 g of 50% solution 0.45 mol) mixed with distilled water (27q) was added to the flask and with stirring over a stir-plate benzal bromide (22.5 g, 0.09 mol, Aldrich) Was also added to 1L. A solution of hydroxylamine sulfate (13.5 g, 0.08% mol) in distilled water (53 g) was then added with mixing through the dropping funnel. The two phase mixture was heated at about 80° C. for 6 hours, when the bottom organic phase completely disappeared. At that point, the content of the flask were cooled and the yellowish solution neutralized with conc. HCl to pH7. A purplish brown organic liquid separated on top. This was collected (11.2 g) and distilled under reduced pressure (105° C. @ 5 mm Hg) and a colorless liquid (10.4 g) was collected yield 95.4%.

The liquid was identified to be benzaldehyde oxime by comparison with authentic sample of the oxime using gas chromatography and Infra Red analyses

EXAMPLE 5

Sodium hydroxide (32 g of 50% solution, 0.4 mol) of mixed with distilled water (25 g) was placed in a 3-necked 250 ml flask fitted with a dropping funnel, thermometer and reflux condenser. A magnetic stirring bar was placed in the flask and the contents stirred over a stir plate. 3-fluorobenzal bromide (21.5 g, 0.08 mol Aldrich) was added to the flask and with further stirring a solution of hydroxylamine sulfate (11 8 g. 0.07 mols) dissolved in distilled water (37 g) was also added. A clear bottom phase was formed by the organic compound. The mixture was stirred and heated from 6 hours at 85° C. and the organic phase slowly disappeared. The clear yellowish aqueous solution was then cooled and neutralized with conc. HCl to pH7. A purplish solid separated out and this was collected by filtration (10 8 g). This was crystallized from methanol and the colorless crystals (9.9 g) were analyzed by gas chromatography and Infra Red and NMR and identified to be 3-fluorobenzaldehyde oxime. Yield 89.2%.

EXAMPLE 6
(Comparative)

A magnetic stirring bar was placed in a 500 ml 3-neck flask fitted with thermometer, dropping funnel and reflux condenser. Hydroxylamine sulfate solution (100 g of 12% solution; 0.07 mols) was placed ln the flask and mixed with 2,2-dichloropropane (11.3 g; 0.1 mols). While stirring a 50% NaOH solution 16 g; 0.2 mols) was slowly added from the dropping funnel.

The two-phase mixture was heated over a mantle with stirring under reflux (~80° C.) for 6 hours. No noticeable change in the amount of organic phase was observed. Gas chromatographic analysis of the organic phase showed no detectable quantity of acetone oxime. A sample of the aqueous phase was neutralized with hydrochloric acid and extracted with toluene and analyzed using gas chromatography. No measurable amount of acetone oxime was found.

EXAMPLE 7

A 500 ml 3-necked flask was set up as in Example 1 and a solution of hydroxylamine sulfate (34 g; 0.207 mol) in water (150ml) was added. While stirring benzal chloride (32.2 g; 0.20 mol) was added. A 50% solution of sodium hydroxide (100 g; 1.25 mol) was added with stirring over 15 minutes. The temperature rose to 55° C. during the addition, and the mixture remained in two phases. It was then heated with stirring for 5 hours at 80° C. and the organic phase disappeared leaving a brownish aqueous solution.

The aqueous solution (pH 12.8) was neutralized with hydrochloric acid an oily phase of benzaldehyde oxime was formed. This was collected using a separatory funnel. Yield was 24.3 g of 98.2% pure benzaldehyde oxime (98.4%).

What is claimed:

1. A process for preparing an aromatic aldoxime from the corresponding aromatic α,α-dihalide comprising:
   (a) reacting said aromatic α,α-dihalide with a hydroxylamine salt in the presence of sufficient aqueous sodium hydroxide to form the corresponding aromatic aldoxime and to maintain said oxime in solution:
   (b) phase separating an organic phase if present and leaving an aqueous phase containing the oxime formed in (a);
   (c) neutralizing the aqueous phase of (b) and thereby forming a separate phase comprising said oxime;
   (d) recovering the oxime from the separate layer formed in (c).

2. The process of claim 1 wherein said aromatic α,α-dihalide has the formula:

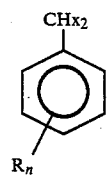

where:
x = Cl, Br, I
R = H, alkyl, alkoxyalkyl, aryl, aralkyl, alkylthio, aryloxy, fluorine perfluoroalkyl
n = 1 to 5

3. The process of claim 2 wherein said aromatic α,α-dihalide is benzal chloride and said oxime is benzaldehyde oxime.

4. The process of claim 1 wherein the hydroxylamine salt is hydroxylamine sulfate.

5. The process of claim 3 wherein said organic phase of (b), comprises impurities in the benzal chloride.

6. The process of claim 1 wherein said neutralization of (c) is done by adding aqueous acid until the pH of the aqueous phase is about 7.

7. The process of claim 6 wherein said aqueous acid is aqueous hydrochloric acid.

8. The process of claim 1 wherein said separate layer of (c) is recovered by phase separation.

9. The process of claim 1 wherein said separate layer of (c) is recovered by solvent extraction.

10. The process of claim 1 wherein the pH of the reaction mixture of (a) is about 9–13.

11. The process of claim 10 wherein the pH of the reaction mixture of (a) is about 12.

12. The process of claim 1 wherein the reaction is carried out at a temperature of 50°–80° C.

* * * * *